United States Patent [19]

Hayashi et al.

[11] Patent Number: 5,567,606
[45] Date of Patent: Oct. 22, 1996

[54] ANTIFOAMING AGENT FOR FERMENTATION, L-AMINO ACID-PRODUCING MEDIUM AND PRODUCTION PROCESS OF L-AMINO ACIDS

[75] Inventors: Masaharu Hayashi; Yuichi Hioki; Masafumi Shonaka; Tadashi Moriyama, all of Wakayama, Japan

[73] Assignee: Kao Corporation, Tokyo, Japan

[21] Appl. No.: 395,656

[22] Filed: Feb. 28, 1995

Related U.S. Application Data

[63] Continuation of Ser. No. 36,281, Mar. 24, 1993, abandoned.

[30] Foreign Application Priority Data

| Apr. 10, 1992 | [JP] | Japan | 4-090723 |
| May 12, 1992 | [JP] | Japan | 4-118898 |
| Aug. 7, 1992 | [JP] | Japan | 4-211698 |

[51] Int. Cl.$^6$ .............. C12P 13/04; C09K 3/00; C07C 51/43
[52] U.S. Cl. .......... 435/106; 435/812; 252/351; 252/182.27; 252/358; 554/168; 554/227
[58] Field of Search .............. 554/168, 227; 252/351, 182.27, DIG. 1; 435/106, 812

[56] References Cited

U.S. PATENT DOCUMENTS

| 2,441,555 | 5/1948 | Barth et al. | 554/227 |
| 3,268,593 | 8/1966 | Carpenter et al. | 252/352 |
| 3,634,472 | 1/1972 | Mills | 554/227 |
| 4,066,558 | 1/1978 | Shay et al. | 252/DIG. 1 |
| 4,070,298 | 1/1978 | Scardera et al. | 252/89 R |
| 4,624,803 | 11/1986 | Balzer et al. | 252/DIG. 1 |
| 4,895,681 | 1/1990 | Herrmann et al. | 554/227 |
| 4,968,448 | 11/1990 | Svarz | 252/358 |

OTHER PUBLICATIONS

Nippin Oils and Fats Co., Ltd., "Additive for L-quitamic Acid Fermentation", *Chemical Abstracts*, 94:190310n 1981.

*Primary Examiner*—Michael G. Wityshyn
*Assistant Examiner*—Francisco C. Prats
*Attorney, Agent, or Firm*—Oblon, Spivak, McClelland, Maier & Neustadt, P.C.

[57] ABSTRACT

Disclosed herein are antifoaming agents for fermentation which include, as active ingredient at least one of (a) a reaction product obtained by adding at least one alkylene oxide to a mixture of a fat and/or oil with a trihydric or still higher polyhydric alcohol, or (b) a compound represented by the following general formula (1):

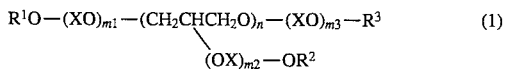

wherein n stands for a number of 2–50, $R^1$, $R^2$ and $R^3$ mean individually a hydrogen atom or an acyl group having 2–31 carbon atoms, x denotes an alkylene group having 2–4 carbon atoms, and m1, m2 and m3 are individually a number of 0–200, an L-amino acid-producing medium containing either one of these components, and a production process for L-amino acids making use of this medium. The use of this antifoaming agent permits the quick, sure and durable suppression of bubbling during incubation, and the overall production of the L-amino acid is significantly improved.

7 Claims, No Drawings

ANTIFOAMING AGENT FOR FERMENTATION, L-AMINO ACID-PRODUCING MEDIUM AND PRODUCTION PROCESS OF L-AMINO ACIDS

This application is a continuation of application Ser. No. 08/036,281, filed on Mar. 24, 1993, now abandoned.

BACKGROUND OF THE BACKGROUND

1. Field of the Invention

The present invention relates to an antifoaming agent for use in fermentation processes, a fermentation medium which incorporates the antifoaming agent, a method of producing L-amino acids in the presence of the agent, and a method of defoaming using the agent.

2. Description of the Background Art

In the fermentative production of useful substances by submerged aerobic culture, a great number of bubbles and foam occur causing various problems. For example, when a fermenter becomes filled with bubbles the culture capacity per unit volume is lowered, and the culture solution can overflow.

Attempts to suppress such bubbling have included the addition of an antifoaming agent to the fermentation medium Polyoxyalkylene polyhydric alcohol ethers, polyoxyalkylene alkyl ethers, polyoxyalkylene fatty acid esters, polyoxyalkylene alkyl ether fatty acid esters, etc. are antifoaming agents previously used (Japanese Patent Application Laid-Open Nos. 4282/1975, 121482/1975, 135298/1979, 169583/1981 and 35073/1990). These antifoaming agents for fermentation baths have not proven very satisfactory, however, due to an unacceptable antifoaming effect, an adverse affect on fermentative production (inhibition of growth of microorganisms, inhibition of formation of products, etc.), a long incubation time before developing an antifoaming effect, or the inability to retain an antifoaming effect over long periods of time.

Since the fermentative production of L-amino acids such as L-glutamic acid, L-lysine, L-glutamine, L-arginine, L-phenylalanine, L-threonine, L-isoleucine, L-histidine, L-proline, L-valine, L-serine, L-ornithine, L-citrulline, L-tyrosine, L-tryptophan and L-leucine is commercially important, is carried out on an industrial scale by the fermentation of microorganisms belonging to Brevibacterium, Corynebacterium, Microbacterium, Bacillus, Escherichia or the like and encounters problems due to foam and bubbles, it is desirable to provide an antifoaming agent that overcomes the above drawbacks.

Further, conventional L-amino acid fermentation processes are unsatisfactory with respect to yield. In order to increase the yield, specific surfactants have been added to the fermentation medium so as to allow for continuous fermentation while crystallizing out the L-amino acid product (Japanese Patent Application Laid-Open No. 288/1977). However, this process has proven unsatisfactory with respect to overall yield, although improvement as compared with conventionally-known processes is obtained.

SUMMARY OF THE INVENTION

It is therefore an object of the present invention to provide an antifoaming agent for fermentation which has excellent antifoaming effects when added to a fermentative medium while improving the yield of the L-amino acid produced, and a process of producing L-amino acids using the medium containing the additive.

The present inventors have found that when a small amount of a product obtained by adding an alkylene oxide to a mixture of a fat and/or an oil with a polyhydric alcohol, or an acylation product of an (alkylene oxide-added) polyglycerol, is added to a fermentative medium, antifoaming is achieved quickly and for extended periods, and that the use of this antifoaming medium in the fermentation of L-amino acids improves the yield of L-amino acids significantly.

In one aspect of the present invention an antifoaming agent for fermentation is provided comprising, as active ingredient(s), either (a) at least one reaction product obtained by adding at least one alkylene oxide to a mixture of a fat and/or an oil with a trihydric or still higher polyhydric alcohol, or (b) at least one compound represented by the following general formula (1):

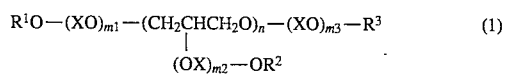

(1)

wherein n stands for a number of 2–50, $R^1$, and $R^3$ mean individually a hydrogen atom or an acyl group having 2–31 carbon atoms, X denotes an alkylene group having 2–4 carbon atoms, and m1, m2 and m3 are individually a number of 0–200, or (c) a mixture of (a) and (b).

In another aspect of the present invention, there is provided an L-amino acid-producing medium comprising water and, optionally a micoorganism, nutrients and salts, and at least one of (a) the reaction product or (b) compound (1), or a mixture of (a) and (b).

In another aspect of the present invention, there is provided a process for the production of an L-amino acid comprising incubating L-amino acid-producing microorganisms in a medium containing at least one of (a) the reaction product or (b) compound (1), or both, and collecting the L-amino acid from the resulting cultured mixture.

Finally, the present invention provides a method of defoaming wherein at least one of (a), the reaction product or (b), a compound of formula (1), or both, are added to a medium which would be expected to foam or to a medium having foam already present.

The use of (a) the reaction product or (b) compound (1), or both, permits the quick, sure and durable suppression of bubbling during incubation. Therefore, the yield of the fermentation product intended per unit fermenter is improved.

In particular, when the above antifoaming agent is added to an L-amino acid-producing medium to produce an L-amino acid, the productivity of the L-amino acid is remarkably improved.

DETAILED DESCRIPTION OF THE PREFERRED EMBODIMENTS

Component (a) useful in the practice of the present invention is the reaction product obtained by adding one or more alkylene oxides to a mixture of at least one fat and/or oil with at least one trihydric or still higher polyhydric alcohol. Examples of the fat or oil used as a raw material herein include vegetable oils such as coconut oil, palm oil, olive oil, soybean oil, rapeseed oil, linseed oil and castor oil; animal oils such as lard, beef tallow and bone oil; fish oils; and hardened oils and partially hydrogenated oils thereof, as well as recovered oils obtained in the purification process of these fats and oils.

Any generally-known alcohol containing three or more —OH groups may be used as the trihydric or still higher polyhydric alcohol. Among these, however, tri- to hexahydric alcohols having 3–15 carbon atoms, such as glycerol, sorbitol, glucose, trimethylolpropane, trimethylolethane, 1,2,4-butanetriol, 1,2,6-hexanetriol, 1,1,1-trimethylolhexane, pentaerythritol, erythrose, tetramethylolcyclohexanol, diglycerol and polyglycerol are preferred and may be used singly or in combination. Of these, glycerol is particularly preferred.

Examples of the alkylene oxide useful herein include ethylene oxide, propylene oxide and butylene oxide. These alkylene oxides may be added either singly or in any combination thereof. It is however preferred that two or more of these alkylene oxides should be added in combination. Examples of the combination of two or more alkylene oxides include ethylene oxide-propylene oxide, ethylene oxide-butylene oxide, and ethylene oxide-propylene oxide-butylene oxide. In the combination of ethylene oxide and propylene oxide or butylene oxide, it is desirable that the number of moles of the added propylene oxide or butylene oxide should be more than that of the added ethylene oxide. The addition of the alkylene oxides may be conducted either by adding them as a mixture (random addition) or by successively adding them (block addition). The total number of moles of the alkylene oxides added is preferably 1–100 moles, more preferably 5–100 moles, most preferably 5–50 moles per mole of the mixture of the fat and/or oil with the polyhydric alcohol. The mixing proportion of the fat or oil with the polyhydric alcohol is preferably 1:0.1–1:6, more preferably 1:0.3–1:3 by mole.

No particular limitation is imposed on the addition reaction of the alkylene oxide, fat and/or oil and polyhydric alcohol. The reaction may be conducted under the general conditions of addition reactions of an alkylene oxide to an active hydrogen-containing compound. More specifically, the reaction may be conducted by adding a catalytic amount of an alkaline substance to a mixture of the fat and/or oil with the polyhydric alcohol, which materials have been charged in the above-described molar ratio, and reacting 1–3 kg/cm$^2$ of the alkylene oxide with the charged mixture at about 100°–200° C.

Examples of component (b), i.e., the compound of formula (1), useful in the practice of the present invention include polyglycerol, mono-, di- and triacylated products of polyglycerol, adducts of polyglycerol with a polyoxyalkylene, and mono-, di- and triacylated products of adducts of polyglycerol with a polyoxyalkylene. Other preferred compounds are those where m1, m2 and m3 are from 0 to 100, n is from 2 to 10, $R^1$, $R^2$ and $R^3$ are acyl groups having 4 to 24 carbon atoms, and x is alkylene of 2–4 carbons.

These compounds (1) can be produced by any method known in the art. An example of the production process of polyglycerol includes a process wherein glycerol is subjected to dehydrocondensation at an elevated temperature of 200°–300° C. in the presence of an alkali catalyst. Examples of the alkali catalyst used herein include NaOH, KOH, LiOH, $Na_2CO_3$, $K_2CO_3$, $Li_2CO_3$, CaO and MgO. The degree of polymerization of polyglycerol may be regulated by changing the reaction conditions. However, the resulting polyglycerol is not a single component, but a mixture having a certain molecular weight distribution. For example, the hydroxyl number of the commercialized polyglycerol referred to as hexaglycerol conforms with the calculated chemical formula thereof, but the polymer is in reality a mixture composed of polyglycerols of different polymerization degrees.

The polyglycerol obtained by the above-described method is a yellow or blackish brown liquid having a high viscosity. As its polymerization degree becomes higher, its hue becomes poorer, approaching blackish brown. Therefore, before use the colored polyglycerol is subjected to a decoloring treatment with an adsorbent like activated carbon or activated clay, or to removal of catalyst and decoloring treatment with an ion-exchange resin. Diglycerol, tetraglycerol, hexaglycerol and decaglycerol have been commercialized.

The present adduct of polyglycerol with a polyoxyalkylene may be produced by any known method including a well-known process wherein after adding an alkali catalyst, an alkylene oxide is added to, for example, the polyglycerol obtained in the above-described manner under pressure and heat. Examples of the alkylene oxide to be added include ethylene oxide, propylene oxide and butylene oxide, which have 2, 3 and 4 carbon atoms, respectively. These alkylene oxides may be added either singly, or in combination, as blocks or at random. They are added in an amount of preferably 1–200 moles, more preferably 1–50 moles on the average per mole basis of polyglycerol.

The mono-, di- or triacylated product of polyglycerol, and mono-, di- or triacylated product of an adduct of polyglycerol with a polyoxyalkylene (both products may be called polyglycerol fatty acid esters) can be generally produced by any direct esterification reaction. Various kinds of hydrophilic or lipophilic esters may be obtained by suitably combining polyglycerols of different polymerization degrees with each other and selecting the kind of a fatty acid to be used and the degree of esterification. Therefore, any ester having an HLB as measured by a Davis method of from 1 to 20, more preferably from 2 to 10 in the case of antifoaming agents, and from 10 to 18 in the case of improving the productivity of L-amino acids may be prepared and used.

The esterification reaction is generally conducted at a temperature not lower than 200° C. without using any catalyst or may be conducted in the presence of an alkali catalyst. Sulfite may be added during the reaction as may lipase, etc. Various products are provided by varying the degree of purification according to their end applications intended. The quality of the polyglycerol fatty acid esters produced depends in large part upon the quality of the polyglycerol starting material. This tendency becomes more pronounced as the polymerization degree of the polyglycerol increases.

A preferred material is a polyglycerol condensed-ricinoleic acid ester synthesized by dehydrating ricinoleic acid (castor oil fatty acid) under heat to precondense it for 3–6 minutes and esterifying polyglycerol with the thus-precondensed ricinoleic acid. The reaction conditions are generally the same as those described above for any polyglycerol fatty acid ester.

Reaction product (a) or compound (1) or their mixture may be used directly as an antifoaming agent for fermentation media and fermentation processes or for any other applications where defoaming is desired. However, they may also be mixed with known antifoaming agents before or after use. Reaction product (a) or compound (1) or their mixture may be added to a foaming medium in one to several portions before or after foaming begins. For fermentation media the agents can be added at the beginning of incubation or during incubation. The amount to be added is preferably 0.0001–5 wt. %, more preferably 0.001–2.5 wt. % based on the medium. It is preferable to add the antifoaming agent according to the present invention in an amount of 0.0001–2 wt. %, more preferably 0,001–1.0 wt. % where it is used to exert only an antifoaming effect, or in an amount of 0,001–5 wt. %, more preferably 0.01–5 wt. %, most preferably 0.05–2.5 wt. % where it is expected to improve the fermentative productivity of an L-amino acid in addition to exerting an antifoaming effect.

No particular limitation is imposed on fermentation culturing means to which the antifoaming agent according to the present invention is applied. Examples include aerobic culture, stirring culture, shaking culture and the like, all of which product a great number of bubbles. The fermentative production of an L-amino acid using the above-described components according to the present invention will hereinafter be described.

Upon production of an L-amino acid, at least one of the reaction products (a) or compound (1) or their mixture may be added either to a medium for seed culture or to a medium for principal fermentation. As a medium to which the at least one reaction product (a) and/or the compound (1) is to be added, media generally used in the incubation of L-amino acid-producing bacteria containing a carbon source, a nitrogen source, salts and other additives can be used. In the present invention, examples of the carbon source include carbohydrates such as glucose, dextrose, sucrose, fructose, maltose, crude sugar, fruit sugar, glucose, liquid sugar, cane molasses, beet sugar, blackstrap molasses, tapioca and starch-saccharified liquor; fatty acids such as acetic acid and propionic acid; organic acids such as pyruvic acid, citric acid, succinic acid and malic acid; and alcohols such as ethyl alcohol and butyl alcohol, all of which may be used either singly or in any combination thereof. As the nitrogen source, examples include ammonium salts such as ammonium sulfate, ammonium chloride and ammonium acetate, urea, aqueous ammonia, corn steep liquor, yeast extract, soybean hydrolyzate, peptone, polypeptone, meat extract, and the like. As the salts, phosphates, magnesium salts, calcium salts, potassium salts, sodium salts, iron salts, manganese salts, zinc salts, copper salts and the like may be used. Other metal salts may be further added as needed.

As described above, a surfactant other than (a) or (b) may be added to the fermentative medium to enhance the yield of the L-amino acid. Examples of such surfactants include anionic surfactants such as higher ($C_6$–$C_{25}$) alcohols, sulfates, alkylbenzenesulfonates, alkyl phosphates and dialkyl sulfosuccinates; cationic surfactants such as alkylamines and quaternary ammonium salts; nonionic surfactants such as polyoxyethylene alkyl ethers, polyoxyethylene sorbitan fatty acid esters, sorbitan fatty acid esters, polyoxyethylene fatty acid esters, polyglycerol fatty acid esters, alkylglycosides and ester amides; and ampholytic surfactants such as imidazoline and betaine. Among these, alkylglycosides and ester amides are preferred. These surfactants may be used either singly or in any combination thereof, and are preferably added in an amount within the range of 0.01–2.5% by weight based on the weight of the medium.

Further, antibiotics, vitamins and the like may be added to the fermentative media as needed. Examples of the antibiotics include penicillin, chloramphenicol, erythromycin, streptomycin, kanamycin, oleandomycin, kasugamycin, tetracycline, mitomycin, actinomycin and cycloserine. Among these, penicillin is preferred. Examples of the vitamins include biotin, niacin and thiamin.

No specific limitation is imposed on the microorganisms added to the fermentative medium according to the present invention. Any one or combination of microorganisms may be used so long as they produce an L-amino acid. Specific examples thereof include the following microorganisms:

Corynebacterium:
*Corynebacterium glutamicum, Corynebacterium acetoglutamicum, Corynebacterium acetoacidophilum;*

Microbacterium:
*Microbacterium amnoneaphilum;*

Brevibacterium:
*Brevibacterium acetoacidophilum, Brevibacterium flavum, Brevibacterium lactofermentum, Brevibacterium saccharolyticum, Brevibacterium roseum, Brevibacterium divaricatum;*

Arthobacter:
*Arthobacter citreus;*

Bacillus:
*Bacillus subtilis, Bacillus sphaericus.*

Examples of L-amino acids obtained by incubating the above-mentioned microorganisms in the invention fermentation bath include L-glutomic acid, L-lysine, L-glutamine, L-arginine, L-phenylalanine, L-threonine, L-isoleucine, L-histidine, Lproline, L-valine, L-tyrosine, L-tryptophan, L-leucine, L-serine, L-ornithine and L-citrulline.

The conditions under which the medium according to the present invention is used to incubate L-amino acid-producing bacteria are the same as those used in general amino acid fermentation. Although the incubation temperature somewhat varies according to the L-amino acid intended and the strain to be used, it may be 20°–40° C. with 28°–37° C. being particularly preferred. Better results are obtained when pH is controlled near neutrality during the incubation. The incubation is generally conducted under aerobic conditions such as aeration, stirring or shaking culture. The incubation period is generally 1–7 days. However, incubation may be extended further by continuous culture or the like. The isolation of L-amino acids from the respective fermented solutions containing the L-amino acids is conducted by ion exchange treatment or any other method known in the art.

EXAMPLES

The present invention will hereinafter be described in more detail by the following examples. However, it should be borne in mind that this invention is not limited to or by these examples.

Example 1

100 ml of media (sterilized at 121° C. for 10 minutes, pH: 7.2) having the composition shown in Table 1 were inoculated with *Brevibacterium flavum* and separately placed in fermenters (500-ml graduated cylinder) and aerated at a rate of 5 l/min. When bubbles reached a marked line at 400 ml, reaction product (a) antifoaming agents shown in Table 2 were separately added little by little to the media which were then incubated at 30° C. for 2 hours. The amounts of the antifoaming agents required to suppress the bubble level at the marked line or lower are shown in Table 2 where the antifoaming agent ratios are by weight.

TABLE 1

| | | | |
|---|---|---|---|
| Glucose | 10% | $FeSO_4.7H_2O$ | 10 μg/l |
| Meat extract | 0.5% | $MnSO_4.nH_2O$ | 10 ng/l |
| Ammonium sulfate | 3% | $CuSO_4.5H_2O$ | 1 mg/l |
| $K_2HPO_4$ | 0.05% | Urea | 0.5% |
| $KH_2PO_4$ | 0.15% | $CaCO_3$ | 3% |
| $MgSO_4.7H_2O$ | 0.05% | Thiamin hydrochloride | 0.5 mg/l |

TABLE 2

| | Antifoaming agent | Amount of anti-foaming agent used (g) |
|---|---|---|
| Inventive examples: | | |
| 1 | Beef tallow/glycerol/EO(5)/PO(15) = 1/0.3/5/15 | 0.010 |
| 2 | Coconut oil/glycerol/EO(10)/PO(30) = 1/0.6/10/30 | 0.013 |
| 3 | Soybean oil/glycerol/EO(15)/PO(25) = 1/1/15/25 | 0.016 |
| 4 | Beef tallow/pentaerythritol/EO(10)/PO(45) = 1/0.5/10/45 | 0.019 |
| Comparative examples: | | |
| 5 | Polypropylene glycol | 1.250 |
| 6 | EO/PO/EO ("Pluronic", product of Asahi Denka Kogyo K.K. | 1.350 |
| 7 | Oleyl alcohol/EO/PO = 1/10/15 | At least 2.5 |
| 8 | Stearic acid/PO = 1/15 | At least 2.5 |

EO: Ethylene oxide; PO: Propylene oxide

As apparent from Table 2, the antifoaming agents according to the present invention exhibit an excellent antifoaming effect in extremely small amounts.

Example 2

A medium containing 10% (in terms of sugar) of blackstrap molasses, 0.5% of urea and 0.3% of corn steep liquor was inoculated with *Corynebacterium glutamicum* and incubated at 30° C. In the prophase of the logarithmic growth phase, 0.15% of polyoxyethylene monopalmitate was added to the medium and incubation conducted at 30° C. for 30 hours.

Thereafter, 15-ml portions of the resulting cultured mixtures were separately placed in 500-ml graduated cylinders. Air was introduced into the cylinders at a rate of 5 l/min. When bubbles reached a marked line at 400 ml, the antifoaming agents shown in Table 2 were added in amounts of 0.001 g to the respective medium portions. After aerating for 30 more minutes, the height (ml) of bubbles occurred in each graduated cylinder was measured. The results are shown in Table 3.

TABLE 3

| Antifoaming agent No. | Height of bubbles (ml) |
|---|---|
| 1 | 150 |
| 2 | 170 |
| 3 | 160 |
| 4 | 200 |
| 5 | At least 500 |
| 6 | 480 |
| 7 | At least 500 |
| 8 | At least 500 |

In the case of Antifoaming Agents Nos. 5, 7 and 8, bubbles overflowed the respective graduated cylinders.

Example 3

An L-lysine-producing medium was prepared as follows:

| | |
|---|---|
| Glucose | 10% |
| $(NH_4)_2SO_4$ | 4.5% |
| Thiamine hydrochloride | 200 µg/l |
| $K_2HPO_4$ | 0.1% |
| Peptone | 1% |
| Biotin | 50 Mg/l | where % is percent by weight. 100 ml-portions of a medium having the above composition were placed in 500-ml Sakaguchi flasks, sterilized at 120° C. for 15 minutes and then inoculated with the L-lysine-producing bacteria Brevibacterium SP. Thereafter, the antifoaming agents shown in Table 1 were separately added to the medium portions in amounts of 0.05% and 1.0% by weight based on each medium portion and incubation was further conducted at 30° C. for 30 hours. The amounts of L-lysine produced in the respective medium portions were then determined. The results are shown in Table 4.

TABLE 4

| Antifoaming agent No. | Amount added (%) | Amount of L-lysine produced (g/l) |
|---|---|---|
| 1 | 0.05 | 7.0 |
| | 1.0 | 6.8 |
| 2 | 0.05 | 7.2 |
| | 1.0 | 7.1 |
| 3 | 0.05 | 6.9 |
| | 1.0 | 7.0 |
| 4 | 0.05 | 7.5 |
| | 1.0 | 7.2 |
| 5 | 0.05 | 4.5 |
| | 1.0 | 2.1 |
| 6 | 0.05 | 5.2 |
| | 1.0 | 3.0 |
| 7 | 0.05 | 4.8 |
| | 1.0 | 3.1 |
| 8 | 0.05 | 4.0 |
| | 1.0 | 1.9 |

As apparent from the results in Table 4, the antifoaming agents according to the present invention (Nos. 1–4) are excellent antifoaming agents each improving the production of L-lysine, a fermentation product.

Example 4

A medium composed of the following composition is prepared by weight.

| | |
|---|---|
| Blackstrap molasses | 4% |
| $KH_2PO_4$ | 0.2% |
| $MgSO_4$ | 0.05% |
| Urea | 0.8% |
| Biotin | 5 µg/l |
| Water | Balance | and adjusted to pH 7.2 with KOH, and a 30-ml portion thereof was placed in a 500-ml Sakaguchi flask and sterilized under heat. This medium portion was inoculated with *Corynebacterium glutamicum* grown on a glucose-peptone slant to conduct preliminary incubation at 30° C. for 18 hours.

Separately, 30-ml portions of a medium (pH: 7–8) having the following composition:

| | |
|---|---|
| Blackstrap molasses | 10% |
| Urea | 1.0% |
| $KH_2PO_4$ | 0.1% |
| $MgSO_4$ | 0.05% |

| | Water | Balance |
|---|---|---| were placed in 500-ml Sakaguchi flasks and sterilized under heat. Medium samples were then prepared by separately adding to each of these 30-ml portions 0.3% by weight of reaction products (a) shown in Table 5, or 0.3% by weight of polyoxyethylene sorbitan monostearate and no additive in comparative examples. 500 μl portions of the preliminarily cultured mixture described above were added to these medium samples having the materials in Table 5 added thereto to conduct shaking culture at 30° C. for 48 hours. The amounts of L-glutamic acid produced in the respective media were then determined and the results are shown in Table 6.

TABLE 5

| | Fat or oil (A) | Alcohol (B) | Molar ratio (A/B) | Alkylene oxide Compound | Mole/ A + B |
|---|---|---|---|---|---|
| Inventive | | | | | |
| 9 | Coconut oil | Glycerol | 1/1 | EO | 20 |
| 10 | Beef tallow | Glycerol | 1/0.5 | EO | 50 |
| 11 | Palm oil | Glycerol | 1/0.5 | EO/PO (Block) | 20/5 |
| 12 | Palm kernel oil | Pentaery- thritol | 1/2 | EO/BO (Block) | 30/10 |
| 13 | Fish oil | Glycerol | 1/0.5 | EO/PO (Random) | 40/5 |
| 14 | Beef tallow | Pentaery- thritol | 1/1 | EO | 20/5 |
| Comp. | | | | | |
| 15 | Polyoxyethylene sorbitan monostearate | | | EO | 20 |
| 16 | Not added | | | — | — |

EO: Ethylene oxide; PO: Propylene oxide; BO: Butylene oxide.

TABLE 6

| | Amount of L-glutamic acid (g/l) |
|---|---|
| 9 | 45.0 |
| 10 | 38.9 |
| 11 | 37.9 |
| 12 | 41.3 |
| 13 | 37.6 |
| 14 | 39.5 |
| 15 | 17.6 |
| 16 | 1.3 |

Example 5

The following media A and B were prepared by weight:

| Medium A: | |
|---|---|
| Blackstrap molasses | 10% (in terms of glucose) |
| (NH$_4$)$_2$SO$_4$ | 4.5% |
| KH$_2$PO$_4$ | 0.1% |
| Peptone | 1% |
| Water | Balance |
| Medium B: | |
| Glucose | 10% |
| Biotin | 50 μg/l |
| Thiamine hydrochloride | 200 μg/l |
| (NH$_4$)$_2$SO$_4$ | 4.5% |
| KH$_2$PO$_4$ | 0.1% |
| Peptone | 1% |
| Water | Balance |

40-ml portions of each of the thus-prepared media were separately poured into two 500-ml Sakaguchi flasks and sterilized. The thus-sterilized portions were inoculated with L-lysine-producing bacteria, Brevibacterium SP and incubation was conducted at 30° C. for 18 hours. 400 μportions of the resulting cultured mixtures were then subcultured into the corresponding media A and B to conduct shaking culture at 30° C. for 8 hours. Thereafter, 0.15% by weight of reaction products (a) shown in Table 7 were separately added to the subcultured media A and B and shaking culture was continued for 24 hours. For the sake of comparison, portions of media A and B which contained 0.15% by weight of polyoxyethylene sorbitan monopalmitate and no additive therein, were incubated in the same manner as described above. The amounts of L-lysine in the cultured mixtures were then determined and the results are shown in Table 8.

TABLE 7

| | Fat or oil (A) | Alcohol (B) | Molar ratio (A/B) | Alkylene oxide Compound | Mole/ A + B |
|---|---|---|---|---|---|
| Inventive | | | | | |
| 17 | Beef tallow | Glycerol | 1/0.5 | EO | 20 |
| 18 | Palm oil | Glycerol | 1/2 | EO/PO (Block) | 25/10 |
| 19 | Fish oil | Pentaery- thritol | 1/1 | EO/PO (Block) | 15/15 |
| 20 | Coconut oil | Tri- methylol- propane | 1/0.5 | EO | 20 |
| 21 | Beef tallow | Di- glycerol | 1/1.0 | EO/BO (Block) | 30/15 |
| Comp. | | | | | |
| 22 | Polyoxyethylene sorbitan monopalmitate | | | EO | 20 |
| 23 | Not added | | | — | — |

TABLE 8

| | Amount of L-lysine (g/l) | |
|---|---|---|
| | Medium A | Medium B |
| 17 | 7.2 | 6.5 |
| 18 | 6.9 | 6.2 |
| 19 | 6.5 | 5.9 |
| 20 | 7.8 | 7.0 |
| 21 | 6.7 | 6.0 |
| 22 | 3.5 | 3.2 |
| 23 | 1.6 | 1.4 |

Example 6

A medium composed of the following composition by weight:

| Blackstrap molasses | 4% |
|---|---|
| KH$_2$PO$_4$ | 0.1% |
| MgSO$_4$ | 0.05% |
| Urea | 0.8% |
| Biotin | 5 μg/l |

-continued

| Water | Balance | was adjusted to pH 7.2 with KOH, and a 30-ml portion thereof was placed in a 500-ml Sakaguchi flask and sterilized under heat. This portion was inoculated with *Corynebacterium glutamicum* grown on a glucose-peptone slant to conduct incubation at 30° C. for 18 hours.

Separately, 30-ml portions of a medium (pH: 7–8) composed of the following composition:

| Blackstrap molasses | 10% (in terms of sugar) |
| Urea | 1.0% |
| $K_2HPO_4$ | 0.1% |
| $MgSO_4$ | 0.05% |
| Water | Balance | were placed in four 500-ml Sakaguchi flasks and sterilized under heat to prepare four media A, B, C and D. Then, 300 μl portions of the cultured mixture obtained above were separately subcultured into media A–D. Further, 0.2% of polyglycerol monolaurate and 0.2% of polyoxyethylene sorbitan monostearate were added to the medium A, 0.3% of polyglycerol monolaurate to the medium B, and 0.3% of polyoxyethylene sorbitan monostearate to the medium C. Medium D had no additive.

The media A–D were separately subjected to shaking culture at 30° C. for 48 hours to determine the amounts of L-glutamine in the respective media. The results are shown in Table 9.

TABLE 9

| Medium | Amount of L-glutamine (g/l) |
| --- | --- |
| Inventive: | |
| A | 39.5 |
| B | 34.0 |
| Comparative: | |
| C | 18.0 |
| D | 1.2 |

Example 7

The following media A and B were prepared by weight:

| Medium A: | |
| --- | --- |
| Blackstrap molasses | 10% (in terms of glucose) |
| $(NH_4)_2SO_4$ | 4.5% |
| $KH_2PO_4$ | 0.1% |
| Peptone | 1% |
| Water | Balance |
| Medium B: | |
| Glucose | 10% |
| Biotin | 50 μg/l |
| Thiamine hydrochloride | 200 mg/l |
| $(NH_4)_2SO_4$ | 4.5% |
| $KH_2PO_4$ | 0.1% |
| Peptone | 1% |
| Water | Balance |

40-ml portions of the thus-prepared media were separately poured into two 500-ml Sakaguchi flasks and sterilized. The thus-sterilized medium portions were inoculated with L-lysine-producing bacteria, Brevibacterium SP to conduct incubation at 30° C. for 18 hours. 400 μl of the resulting cultured mixtures were subcultured into their corresponding media A and B to conduct shaking culture at 30° C. for 8 hours. Thereafter, 0.15% of polyglycerol stearate was added to subcultured media A and B to continue the shaking culture further for 24 hours. For the sake of comparison, portions of media A and B, which contained no polyglycerol stearate therein, were incubated in the same manner as described above. The amounts of L-lysine produced in the respective cultured mixtures thus obtained are shown in Table 10.

TABLE 10

| Medium | Agent for improving the yield of amino acid | Amount of L-lysine (g/l) |
| --- | --- | --- |
| A | Added | 7.2 |
|   | Not added | 1.8 |
| B | Added | 6.0 |
|   | Not added | 1.9 |

What is claimed is:

1. A method of reducing the tendency of an aqueous fermentation medium to foam, comprising:

adding to the aqueous fermentation medium a defoaming agent which is the reaction product obtained by reacting at least one alkylene oxide selected from the group consisting of ethylene oxide, propylene oxide, butylene oxide or mixtures thereof with a mixture of (1) at least one vegetable oil or animal oil and (2) a trihydric or higher polyhydric alcohol, said reaction product having a fatty acid content as low as the beef tallow component of the composition: beef tallow/pentaerythritol/ethylene oxide/propylene oxide in a mole ratio of 1:0.5:10:45 to as high as the coconut oil content of the composition: coconut oil/glycerol/ethylene oxide in a mole ratio of 1:1:20.

2. The method of claim 1, wherein said at least one vegetable oil or animal oil is a hardened oil or partially hydrogenated oil thereof or is an oil recovered by purification of said vegetable oil or animal oil.

3. The method of claim 2, wherein the mixing proportion of the fat and/or oil and the trihydric or higher polyhydric alcohol in the reaction product is 1:0.1–1:6 by mol.

4. The method of claim 3, wherein said mixing proportion is 1:0.3–1:3.

5. The method of claim 1, wherein the reaction product is added to the aqueous fermentation medium in an amount of 0.05–2.5 weight % based on the medium.

6. The method of claim 1, which further comprises adding at least one L-amino acid producing microorganism to the aqueous fermentation medium.

7. The method of claim 6, wherein the at least one microorganism is selected from the group consisting of *Corynebacterium glutamicum, Corynebacterium acetoglutamicum, Corynebacterium acetoacidophilum, Microbacterium ammoniophilum, Brevibacterium acetoacidophilum, Brevibacterium lactofermentum, Brevibacterium flavum, Brevibacterium saacharolyticum, Brevibacterium roseum, Brevibacterium divaricatum, Arthobacter citreus, Bacillus subtilis* and *Bacillus sphaericus.*

* * * * *